United States Patent [19]

Miller et al.

[11] Patent Number: 5,028,312

[45] Date of Patent: Jul. 2, 1991

[54] METHOD OF DEHYDROCYCLIZING ALKANES

[75] Inventors: Jeffrey T. Miller; Frank S. Modica; Victor K. Shum, all of Naperville, Ill.

[73] Assignee: Amoco Corporation, Chicago, Ill.

[21] Appl. No.: 359,138

[22] Filed: May 31, 1989

[51] Int. Cl.$^5$ ............................................. C10G 35/085
[52] U.S. Cl. ...................................................... 208/138
[58] Field of Search ......................................... 208/138

[56] References Cited

U.S. PATENT DOCUMENTS

| | | | |
|---|---|---|---|
| 4,456,527 | 6/1984 | Buss et al. | 208/138 |
| 4,634,518 | 1/1987 | Buss et al. | 208/138 |
| 4,645,588 | 2/1987 | Buss et al. | 208/138 |

Primary Examiner—Curtis R. Davis
Attorney, Agent, or Firm—Reginald K. Taylor; William H. Magidson; Ralph C. Medhurst

[57] ABSTRACT

A method is disclosed for reforming hydrocarbons, particularly $C_6$–$C_{10}$ hydrocarbons, to aromatics, by passing the hydrocarbons over a dehydrocyclization catalyst at dehydrocyclization conditions. The catalyst comprises a non-acidic large pore zeolite having a Group VIII metal and an alkaline earth metal, said alkaline earth metal having been impregnated onto the zeolite by contacting the zeolite with an alkaline earth metal solution of a concentration sufficient to result in the zeolite having an alkaline earth metal content of less than about 2% by weight of the zeolite.

5 Claims, No Drawings

METHOD OF DEHYDROCYCLIZING ALKANES

BACKGROUND OF THE INVENTION

The invention pertains to a method of dehydrocyclizing alkanes comprising paraffins containing at least six carbon atoms.

Higher octane gasolines permit the building of engines that extract more power from gasoline. The demand for high octane gasoline has resulted in a substantial increase for the use of catalytic reforming. In catalytic reforming, the structures of the hydrocarbon molecules are rearranged to form higher octane aromatics.

The typical catalytic reformer feedstock is composed of paraffins, olefins, naphthenes, and aromatics. The four major reforming reactions that occur during catalytic reforming are: (1) dehydrogenation of naphthenes to aromatics, (2) dehydrocyclization of paraffins to aromatics, (3) isomerization, and (4) hydrocracking.

Hydrocracking reactions result in the production of lighter liquid and gas products. These relatively slow exothermic reactions occur in the latter section of the reactor. The major hydrocracking reactions involve the cracking of paraffins. These reactions are to be avoided during reforming because they decrease the yield of gasoline boiling products and, since hydrocracking is an exothermic process, they generally are accompanied by severe temperature excursions which can result in temperature increases in a reforming operation.

Isomerization of paraffins and naphthenes usually results in a lower octane product than conversion to aromatics; however, there is a substantial increase over that of the unisomerized materials. The isomerization reactions are relatively rapid reactions with small heat effects. An example of such a reaction is the isomerization of normal paraffins to isoparaffins.

The dehydrogenation reactions are highly endothermic and cause a decrease in temperature as the reaction progresses. The basic dehydrogenation reactions are: (1) dehydrogenation of alkylcyclohexanes to aromatics, (2) dehydroisomerization of alkylcyuclopentanes to aromatics, and (3) dehydrocyclization of paraffins to aromatics. Although, the dehydrogenation of cyclohexane derivatives is a faster reaction than either the dehydroisomerization of alkylcyclopentanes or the dehydrocyclization of paraffins, all three reactions are necessary to obtain the high aromatic concentration needed in the product to produce a high octane.

The conventional methods of dehydrocyclizing paraffins to form aromatics are based on the use of "bifunctional" catalysts, so called because they include both a noble metal and an acidic support. As is well known, these catalysts commonly comprise platinum on a chlorided alumina support. Other acidic supports have also been proposed or used, including zeolites X, Y, mordenite, and ZSM-5. The term "zeolite" refers to a group of hydrated, crystalline metal aluminosilicates. Zeolites consist basically of an open three-dimensional frame of $SiO_4$ and $AlO_4$ tetrahedra. The tetrahedra are cross-linked by the sharing of oxygen atoms such that the ratio of oxygen atoms to the total of the aluminum and silicon atoms is equal to 2. The negative electrovalence of tetrahedra containing aluminum is balanced by the inclusion within the crystal of cations, e.g., alkali metals, alkaline earth metals, and hydrogen.

In general, dehydrocyclization is carried out by passing the hydrocarbons to be converted to aromatics over a catalyst in the presence of hydrogen at temperatures ranging from 430°–550° C. and pressures ranging from 100–500 psig. Not all of the hydrocarbons will be converted into aromatics. Some of the paraffins will be converted into isoparaffins and lighter hydrocarbons by the isomerization and cracking reactions. The rate at which the hydrocarbons will be converted into aromatics depends upon the reaction conditions and the nature of the catalyst. Catalysts used in the past have been successful in converting $C_8$-$C_{11}$ paraffins into aromatics; however, these catalysts have shown less than satisfactory results with $C_6$-$C_7$ paraffins, particularly $C_6$ paraffins.

In another method of dehydrocyclizing paraffins, "monofunctional" catalysts are used, so called because they contain a noble metal on a support which is substantially non-acidic. In one such method, described in U.S. Pat. No. 4,447,316, the hydrocarbon containing feed is passed in the presence of hydrogen at a temperature of 430°–550° C. over a type L zeolite catalyst having an alkaline earth metal cation and at least one metal from Group VIII of the Periodic Table. In this method, the alkaline earth metal cation was added to the type L zeolite by using an ion exchange. In this ion exchange method, the type L zeolite, having substantially all of its cationic exchange sites occupied by potassium ions, is contacted with a solution containing a soluble barium salt, e.g. barium nitrate. Typical ion exchange requires a large excess, up to 5 times the ion exchange capacity, of $Ba^{+2}$ During this contacting, some of the barium ions exchange places with some of the potassium ions. The solution, carrying the potassium ions exchanged from the zeolite and the unexchanged barium ions, is then separated from the zeolite, for example by filtration. This filtered solution of excess $Ba^{+2}$ creates an additional disposal or recovery problem. Using this method, the barium can replace up to about 70% of the potassium originally in the zeolite.

There is a need for a method of dehydrocyclizing alkanes using a non-acidic large pore zeolite catalyst with improved activity and selectivity for converting $C_6$-$C_{10}$ hydrocarbons to aromatics. There is also a need for a method of dehydrocyclizing alkanes using a non-acidic large pore zeolite catalyst that does not require a large excess of barium ions to prepare the catalyst, thereby avoiding the additional cost of disposing of excess barium solutions.

SUMMARY OF THE INVENTION

The present invention is a method of reforming hydrocarbons using a catalytic reforming reactor loaded with a catalyst comprising a non-acidic large pore zeolite having a Group VIII metal such as platinum and an alkaline earth metal such as barium. An essential element of this invention is impregnating the alkaline earth metal onto the zeolite by contacting the zeolite with an alkaline earth metal solution of a concentration sufficient to result in a zeolite having an alkaline earth metal content of less than about 2% by weight of the zeolite. The first step of the present invention is to introduce hydrogen into the reactor to prereduce the platinum non-acidic large pore platinum zeolite catalyst. The next step is to contact the hydrocarbons with the non-acidic large pore platinum zeolite catalyst at reforming conditions comprising a temperature of 850°–1000° F., a pressure of 50–200 psi, a weight space velocity of 0.1–5 hr-1, and a hydrogen/hydrocarbon mole ratio of 0.5–4.

DESCRIPTION OF THE PREFERRED EMBODIMENT

The present invention encompasses a method for dehydrocyclizing paraffins, particularly $C_6-C_{10}$, to form aromatics by passing hydrocarbons containing the paraffins over a catalyst. The catalyst comprises a non-acidic large pore zeolite having a Group VIII metal and having an alkaline earth metal content of less than 2% by weight, said alkaline earth metal being added to the zeolite by impregnation. This method of dehydrocyclizing uses a catalyst that has a higher activity and higher selectivity for converting $C_6-C_{10}$ hydrocarbons to aromatics than previous dehydrocyclization catalyst.

Selectivity, as used in the present invention, is defined as the percentage of moles of paraffin converted to aromatics relative to moles of paraffin converted. The selectivity for converting paraffins to aromatics is a measure of the efficiency of the process in converting paraffins to the desired products of aromatics and hydrogen.

Highly selective catalysts have several advantages. First, higher aromatics give higher yields of higher octane. Second, such catalysts produce more hydrogen than less selective catalysts. Since hydrogen is produced when converting paraffins to aromatics and consumed when paraffins are converted to cracked products, an increase in the selectivity of the process increases the amount of hydrogen produced and decreases the amount of hydrogen consumed. Third, highly selective catalysts produce purer hydrogen. The purity of the hydrogen produced in reforming operations is important because the hydrogen is normally used in other processes, such as hydrotreating and hydrocracking which require a minimum partial pressure of hydrogen.

Activity is defined in this invention as a relative assessment of how much catalyst is needed to result in a certain conversion of paraffins to aromatics at constant operating conditions. Relative catalyst activity can be determined by taking a ratio of space velocities of different catalysts to give constant conversion, for example, at constant temperature, pressure, and hydrogen to hydrocarbon ratio.

An essential feature of the catalyst used in the present invention is that it comprises a non-acidic large pore zeolite. This means that substantially all of the cationic sites of exchange on the zeolite are occupied by non-hydrogen cationic species. Regardless of the actual cationic species in the cationic sites, the non-acidic large pore zeolite in the present invention has substantially all of the cationic sites occupied by non-hydrogen cations, especially Group I and Group II, thereby rendering the zeolite substantially fully cationic exchanged.

Examples of non-acidic zeolites suitable for use in the present invention are Na X zeolite, Na Y zeolite, and K L zeolite. These zeolites are known as large pore zeolites. Their effective pore diameters are 6-8 Angstroms.

The composition of type L zeolite expressed in terms of mole ratios of oxides may be represented as follows:

$$(0.9-1.3)K_2O:Al_2O_3(5.2-6.9)SiO_2:(0-9)H_2O \quad (1)$$

Zeolite L, its properties, and a method for its preparation are described in U.S. Pat. No. 3,216,789.

The chemical formula for zeolite Y expressed in mol oxides can be written as:

$$(0.7-1.1)Na_2O:Al_2O_3:(3.0-6.0)SiO_2:(0-9)H_2O \quad (2)$$

Zeolite Y has a characteristic x-ray powder diffraction pattern which may be employed with the above formula for identification. Zeolite Y is described is U.S. Pat. No. 3,130,007.

Zeolite X is a synthetic crystalline zeolitic molecular sieve which can be represented by the following formula:

$$(0.7-1.1)Na_2O:Al_2O_3:(2.0-3.0)SiO_2:(0-8)H_2O \quad (3)$$

Zeolite X, its properties, and a method for its prepartion are described in U.S. Pat. No. 2,882,244.

As indicated above, the cations occupying the cationic exchangeable sites are non-hydrogen species. Initially, these non-hydrogen species are alkali metals, such as sodium or potassium. Accordingly, the non-acidic large pore zeolite of the present invention can initially comprise the sodium or potassium forms of X zeolite, Y zeolite, or L zeolite.

An essential feature of the present invention is the use of a dehydrocyclization catalyst comprising a non-acidic large pore zeolite to which has been added an alkaline earth metal, such addition to be carried out by impregnation or other means known to the art so as to deposit the metal on the surface of the zeolite rather than by ion exchange. The concentration of the alkaline earth metal must be less than 2% by weight of the zeolite.

The alkaline earth metal is deposited on the surface of the large pore zeolite by impregnation using an alkaline earth metal salt solution to just fill the pore volume of the zeolite catalyst. By avoiding the ion exchange method of adding the alkaline earth metal to the zeolite, the problems associated with the use of a large excess alkaline earth metal solution can be avoided. One such problem is how to dispose of the excess alkaline earth metal solution. Typically, ion exchange of the alkaline earth metal with the zeolite catalyst requires that the zeolite be refluxed in a large volume of concentrated alkaline earth metal salt solution for several hours. The solution is then filtered off and the zeolite washed. The filtered solution of excess alkaline earth metal creates an additional disposal problem.

The non-acidic large pore zeolite catalyst is preferably bound with a support matrix. Examples of support matrices suitable for use in this invention are clays, bauxite, refractory inorganic oxide such as alumina, zirconium dioxide, hafnium oxide, cesium oxide, titanium dioxid chromium oxide, zinc oxide, magnesia, boria, silica-magnesia, silica, chromia-alumina, and alumina-boria. The non-acidic zeolite may be bound within the support matrix by any method known in the art. Such methods suitable for use in this invention include pilling, extruding, and granulating.

A further essential feature of the catalyst of the present invention is the presence of a Group VIII metal component, including nickel, ruthenium, rhodium, osmium, palladium, iridium, platinum, or any mixture thereof. Especially preferred among the Group VIII metal components is platinum. The Group VIII metal components may be incorporated into the non-acidic large pore zeolite catalyst by any suitable means known in the art. For example, a platinum component may be impregnated by means of an appropriate solution, such as a dilute tetraammine platinum (II) nitrate. Alternatively, the Group VIII metal component may be incorporated by means of ion exchange. The Group VIII metal component may be incorporated with other constituents either prior or subsequent to the deposition of the alkaline earth metal.

After the desired metals have been incorporated into the non-acidic large pore zeolite, the zeolite can be loaded into a catalytic reformer reactor to carry out the conversion of the $C_6$-$C_{10}$ hydrocarbons to aromatics. The catalyst can be disposed as a fixed bed within a reaction zone and the charging stock may be passed therethrough in a liquid, vapor, or mixed phase, and in either upward or downward flow. Alternatively, the catalyst can be employed in moving beds or in fluidized solid processes in which the charging stock is passed upward through a turbulent bed of finely divided catalyst. The reaction products from any of the foregoing processes are separated from the catalyst, vented to the atmosphere, and fractionated to recover the various components thereof.

Once the catalyst has been loaded into the reforming reactor, hydrogen is introduced into the reactor to prereduce the catalyst. Next, the hydrocarbon feed is introduced into the reactor. The feed preferably comprises non-aromatic hydrocarbons ranging from $C_6$-$C_{10}$. Preferably, the feedstock is substantially free of sulfur, nitrogen, metals, and other known poisons for the reforming catalyst.

The dehydrocyclization is carried out in the presence of hydrogen at a pressure adjusted to favor the reaction thermodynamically and limit undesirable hydrocracking reactions. The pressure used ranges from 1–200 psi, preferably from 50–200 psi. The molar ratio of hydrogen/hydrocarbons used ranges from 0.2–10, preferably from 0.5–4.

The temperature range suitable for this invention is 700°–1200° F., preferably 850°–1000° F. If the temperature is below 700° F., the reaction rate is low, and consequently the yield is so low that industrial uses are not practical. On the other hand, operating the temperature above 1200° F. results in secondary reactions, such as hydrocracking and coking which substantially reduce the yield and catalyst life.

A liquid hourly space velocity suitable for use in this invention is 0.1–10, preferably 0.1–5.

EXAMPLE 1

100 gm of barium nitrate was dissolved in 1200 ml of water. 200 gm of Type L zeolite was added. The solution was refluxed for 3 hr and filtered. The zeolite was washed by adding 1200 ml of water, refluxing for 30 min, and filtering. The zeolite was dried at 250° F. 10 gm of the barium-exchanged Type L zeolite was impregnated with 0.24 gm Pt(NH3)4(NO3)2 in 7 ml of water. The catalyst was dried overnight at 250° F. The catalyst contained 1.2% platinum and 7.6% barium.

EXAMPLE 2

To 25 gm of potassium type L zeolite was added 1.0 gm of barium nitrate dissolved in 15 ml of water. The catalyst was dried and then calcined at 850° F. for 1 hr. To 10 gm of the above catalyst was added 0.25 gm of Pt(NH3)4(NO3)2 dissolved in 7 ml of water. The catalyst was dried and further heated to 350° F. for 1 hr. The catalyst contained 1.2% platinum and 2.26% barium.

EXAMPLE 3

To 15 gm of potassium type L zeolite was added 0.50 gm of barium nitrate and 0.36 gm of Pt(NH3)4(NO3)2 dissolved in 10 ml of water. The catalyst was dried and further heated to 350° F. for 1 hr. The catalyst contained 1.2% platinum and 1.23% barium.

EXAMPLE 4

To 10 gm potassium type L zeolite was impregnated 0.4 gm of barium nitrate. The catalyst was dried at 350° F. and calcined at 950° F. 0.25 gm of Pt(NH3)4(NO3)2 was added to the barium impregnated potassium Type L zeolite and dried at 350° F. The catalyst contained 1.2% platinum and 1.99% barium.

EXAMPLE 5

To 10 gm of potassium type L zeolite was impregnated 0.2 gm of barium nitrate. The catalyst was calcined at 950° F. 0.25 gm of Pt(NH3)4(NO3)2 was added to the barium impregnated potassium type L zeolite and dried at 350° F. The catalyst contained 1.2% platinum and 1.11% barium.

EXAMPLE 6

To 20 gm of potassium type L zeolite was impregnated 0.20 gm of barium nitrate. The catalyst was dried at 350° F. To 10 gm of the barium impregnated potassium type L zeolite (uncalcined) was added 0.25 gm of Pt(NH3)4(NO3)2 and dried at 350° F. The catalyst contained 1.2% platinum and 0.67% barium.

EXAMPLE 7

10 gm of barium impregnated potassium type L zeolite from Example 6 was calcined at 950° F. 0.25 gm of Pt(NH3)4(NO3)2 was added and dried at 350° F. The catalyst contained 1.2% platinum and 0.67% barium.

EXAMPLE 8

To 10 gm of potassium type L zeolite was added 0.10 gm of barium nitrate and 0.25 gm of Pt(NH3)4(NO3)2. The catalyst was dried at 350° F. The catalyst contained 1.2% platinum and 0.7% barium.

In Examples 1–8, each of the catalysts was evaluated for conversion of n-hexane to benzene. The reaction conditions were T=750° F., WHSV=1.0 and 2.0 hr$^{-1}$, H2=150 ml/min, P=atmospheric. Catalysts were prereduced at 800° F. Relative catalyst activities were determined by calculating the ratio of space velocity required to give constant conversion. The catalyst in Example 1 was taken at 1.0 relative activity. Table 1 summarizes the activity and selectivity data.

TABLE I

| Catalyst | % Ba | Relative Activity | Benzene Selectivity |
|---|---|---|---|
| ION exchange | | | |
| 1 (reference) | 7.60 | 1.0 | 85 |
| 2 | 2.26 | 0.5 | 93 |
| 3 | 1.23 | 0.4 | 90 |
| 4 | 1.99 | 0.4 | 92 |
| 5 | 1.11 | 1.8 | 92 |
| 6 | 0.67 | 3.6 | 88 |
| 7 | 0.67 | 5.1 | 91 |
| 8 | 0.70 | 4.5 | 90 |

The test results show that highly active and more aromatics selective L-zeolite aromatization catalysts can be made by impregnation with barium nitrate rather than by ion exchange, if the barium loading is kept below about 1%. Impregnated catalysts are also more aromatic selective by 5%. The results also show that superior catalysts can be prepared by single co-impregnation of barium nitrate and $Pt(NH_3)_4(NO_3)_2$. No excess solutions were produced.

That which is claimed is:

1. A method of reforming hydrocarbons using a catalytic reforming reactor loaded with a non-acidic large pore zeolite, comprising the steps of:
   (a) introducing hydrogen into the reactor to prereduce the non-acidic large pore zeolite, said non-acidic large pore zeolite comprising a Group VIII metal and an alkaline earth metal, said alkaline earth metal having been impregnated onto the zeolite by contacting the zeolite with an alkaline earth metal solution of a concentration sufficient to result in the zeolite having an alkaline earth metal content less than 1% by weight of the zeolite; and
   (b) contacting the hydrocarbons with the non-acidic large pore zeolite at a temperature ranging from 850°-1000° F., a pressure ranging from 50-200 psi, a weight space velocity ranging from 0.1-5, and a hydrogen/hydrocarbon mole ratio ranging from 0.5-4.

2. A method of claim 1 wherein the non-acidic large pore zeolite is type L zeolite.

3. A method of claim 2 wherein the alkaline earth metal is barium.

4. A method of claim 3 wherein the Group VIII metal is platinum.

5. A method of reforming hydrocarbons using a catalytic reforming reactor loaded with a reforming catalyst comprising an L zeolite, barium, and platinum, comprising the steps of:
   (a) introducing hydrogen into the reactor to prereduce said catalyst, said barium having been impregnated onto said L zeolite by contacting said L zeolite with a barium solution of a concentration sufficient to result in said catalyst having a barium content of less than about 1% by weight of said L zeolite; and
   (b) contacting said hydrocarbon with said catalyst at a temperature ranging from 850°-1000° F., a pressure ranging from 50-200 psi, a weight space velocity ranging from 0.1-5, and a hydrogen/hydrocarbon mole ratio ranging from 0.5-4.

* * * * *